(12) United States Patent
Van Slyke et al.

(10) Patent No.: US 8,594,759 B2
(45) Date of Patent: Nov. 26, 2013

(54) SYSTEMS AND METHODS FOR RESOLVING THE CONTINUOUS WAVELET TRANSFORM OF A SIGNAL

(75) Inventors: Braddon M. Van Slyke, Arvada, CO (US); Paul Stanley Addison, Edinburgh (GB); James Nicholas Watson, Dunfermline (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1125 days.

(21) Appl. No.: 12/512,113

(22) Filed: Jul. 30, 2009

(65) Prior Publication Data

US 2011/0028810 A1    Feb. 3, 2011

(51) Int. Cl.
*A61B 5/00*    (2006.01)
*G01N 33/48*    (2006.01)
*G01N 33/50*    (2006.01)
*G06F 17/14*    (2006.01)

(52) U.S. Cl.
CPC .................................. *G06F 17/148* (2013.01)
USPC ............................................ 600/323; 702/19

(58) Field of Classification Search
None
See application file for complete search history.

(56) References Cited

U.S. PATENT DOCUMENTS

| | | |
|---|---|---|
| 4,289,141 A | 9/1981 | Cormier |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |

(Continued)

FOREIGN PATENT DOCUMENTS

| | | |
|---|---|---|
| JP | 09-084776 | 3/1997 |
| WO | WO 01/25802 | 4/2001 |

(Continued)

OTHER PUBLICATIONS

Addison, Paul S., The Illustrated Wavelet Transform Handbook, Taylor & Francis Group, 2002.

(Continued)

*Primary Examiner* — Russell S Negin
(74) *Attorney, Agent, or Firm* — Shvarts & Leiz LLP

(57) ABSTRACT

According to an embodiment, techniques for estimating scalogram energy values in a wedge region of a scalogram are disclosed. A pulse oximetry system including a sensor or probe may be used to receive a photoplethysmograph (PPG) signal from a patient or subject. A scalogram, corresponding to the obtained PPG signal, may be determined. In an approach, energy values in the wedge region of the scalogram may be estimated by performing convolution-based or convolution-like operations on the obtained PPG signal, or a transformed version thereof, and the scalogram may be updated according to the estimated values. In an approach, a deskewing technique may be used to align data prior to adding the data to the scalogram. In an approach, one or more signal parameters may be determined based on the resolved and estimated values of the scalogram.

24 Claims, 13 Drawing Sheets

(56) References Cited

U.S. PATENT DOCUMENTS

| | | |
|---|---|---|
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,430,525 B1 | 8/2002 | Weber et al. |
| 6,561,986 B2 | 5/2003 | Baura et al. |
| 6,608,934 B2 | 8/2003 | Scheirer et al. |
| 6,654,623 B1 | 11/2003 | Kastle |
| 6,810,277 B2 | 10/2004 | Edgar, Jr. et al. |
| 6,931,269 B2 | 8/2005 | Terry |
| 6,993,377 B2 | 1/2006 | Flick et al. |
| 6,999,904 B2 | 2/2006 | Weber et al. |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,477,571 B2 | 1/2009 | Melese et al. |
| 7,499,835 B2 | 3/2009 | Weber et al. |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 2005/0043616 A1 | 2/2005 | Chinchoy |
| 2006/0211930 A1 | 9/2006 | Scharf et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

SYSTEMS AND METHODS FOR RESOLVING THE CONTINUOUS WAVELET TRANSFORM OF A SIGNAL

SUMMARY

The present disclosure is related to signal processing systems and methods, and more particularly, to systems and methods for estimating scalogram energy values in a wedge region of a scalogram using convolutional techniques.

In an embodiment, a photoplethysmograph (PPG) signal may be received from a pulse oximetry system, including, for example, from a sensor coupled to the pulse oximetry system. Processing equipment may be used to generate a scalogram from the received PPG signal using, for example, a continuous wavelet transform. In an approach, the received PPG signal may be sampled, and the sampled PPG signal may be convolved with wavelet coefficients. In an approach, any suitable convolution-based or convolution-like technique may be used to perform the convolving, and the convolving may rely on iterative techniques. In an approach, the wavelet coefficients may be stored in a wavelet table, and may represent, for example, a Haar or Morlet wavelet. In an approach, the convolving operation may produce output samples that are skewed in time relative to the scalogram. In an approach, the output samples may be deskewed in time, and the deskewed samples may be added to the scalogram to update the scalogram. In an approach, one or more signal parameters may be determined based on the updated scalogram (which may include both fully resolved scalogram values as well as estimated scalogram values), and the determined signal parameters may be output to an output device, including, for example, a display or monitor device. In an approach, the output device may include an audible alarm.

In an embodiment, estimates of the scalogram may be performed periodically in time, for example, at a predetermined or variable refresh rate. In an approach, the refresh rate may rely on an expected time-rate of change of at least one patient parameter. In an approach, the expected time-rate of change may be determined adaptively or using detection techniques. In an approach, the sampling of the PPG signal may be performed at a constant or at a substantially constant time-rate. In an approach, the sampling may be performed according to the actual and/or expected frequency content of the received PPG signal, and the sampling may be performed at any suitable frequency, for example, at a Nyquist frequency. In an approach, the convolving (i.e., the convolution-based or convolution-like technique), may be performed using a processor or processors, and may rely on matrix multiplications. In an embodiment, the determined signal parameters may relate to a patient respiration rate, a patient oxygen saturation level, a patient respiration effort level, any other suitable parameter, or any combination thereof.

In an embodiment, the degree of resolution to which a wavelet transform of the signal is performed may be determined by an operator. In an approach, a wavelet may have finite extent, and, in this case, the entire wavelet may be used to perform the wavelet transform. Alternatively, the wavelet may have infinite extent, and, in this case, an operator may define a point at which the error between the true wavelet transform and the computed wavelet transform is acceptable for the purposes of the computation. In an approach, an infinite wavelet may be truncated to form a wavelet of finite extent. In an approach, a truncated wavelet may not have zero mean amplitude. For example, the DC component of the wavelet may change as the position at which the wavelet is truncated changes. Therefore, in an approach, this non-zero mean of the wavelet may be compensated for through the inclusion of an additional term or terms in the convolving technique.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
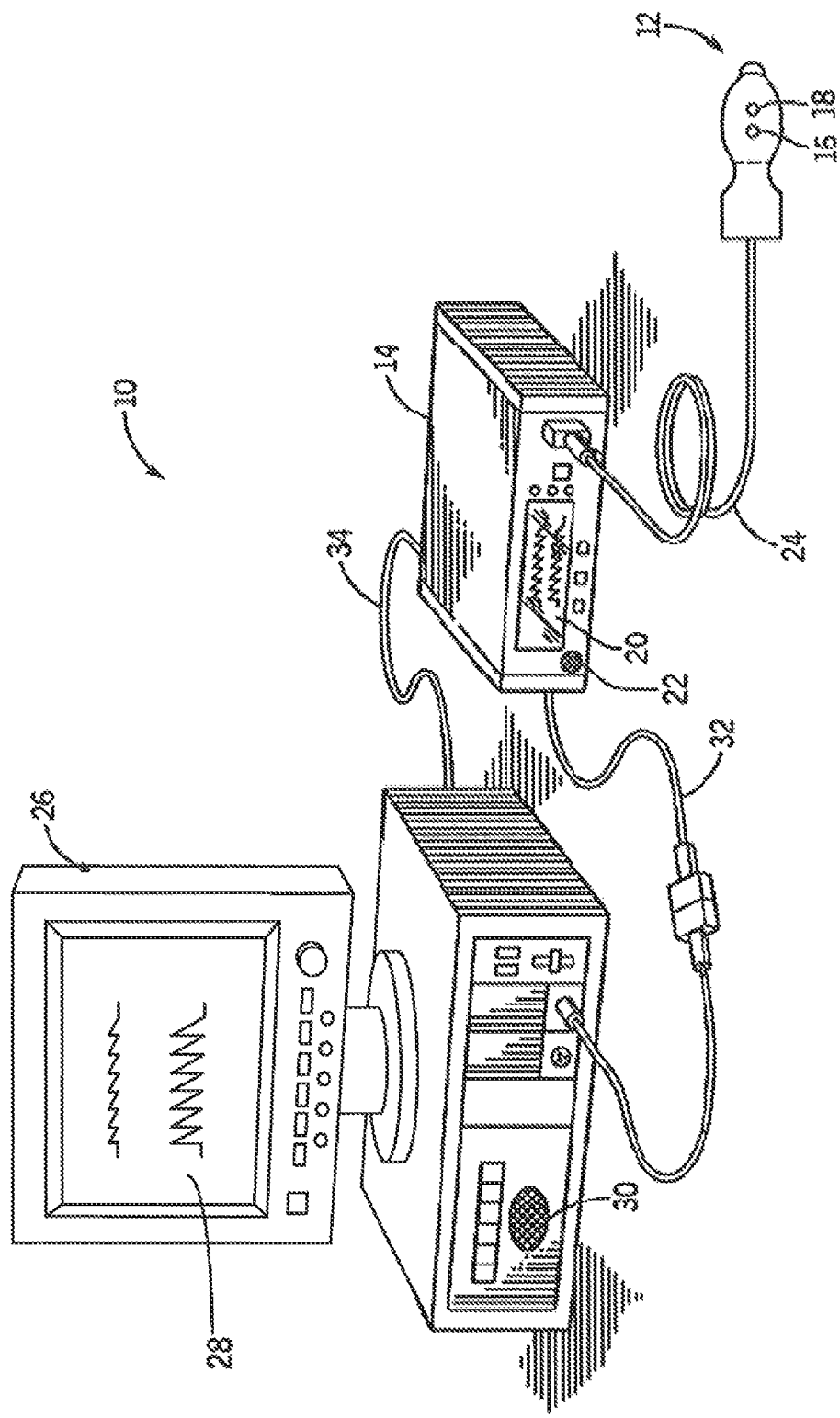
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (that is, representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_0 + (1-s)\beta_r)\frac{dl}{dt} \quad (3)$$

3 Red (3) is divided by IR (3)

$$\frac{d\log I(\lambda_R)/dt}{d\log I(\lambda_{IR})/dt} = \frac{s\beta_0(\lambda_R) + (1-s)\beta_r(\lambda_R)}{s\beta_0(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR})$$

$$y(t)=Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an approach, emitter 16 and detector 18 may be arranged so that light from emitter 16 penetrates the tissue and is reflected by the tissue into detector 18, such as a sensor designed to obtain pulse oximetry data from a patient's forehead.

In an approach, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an approach, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
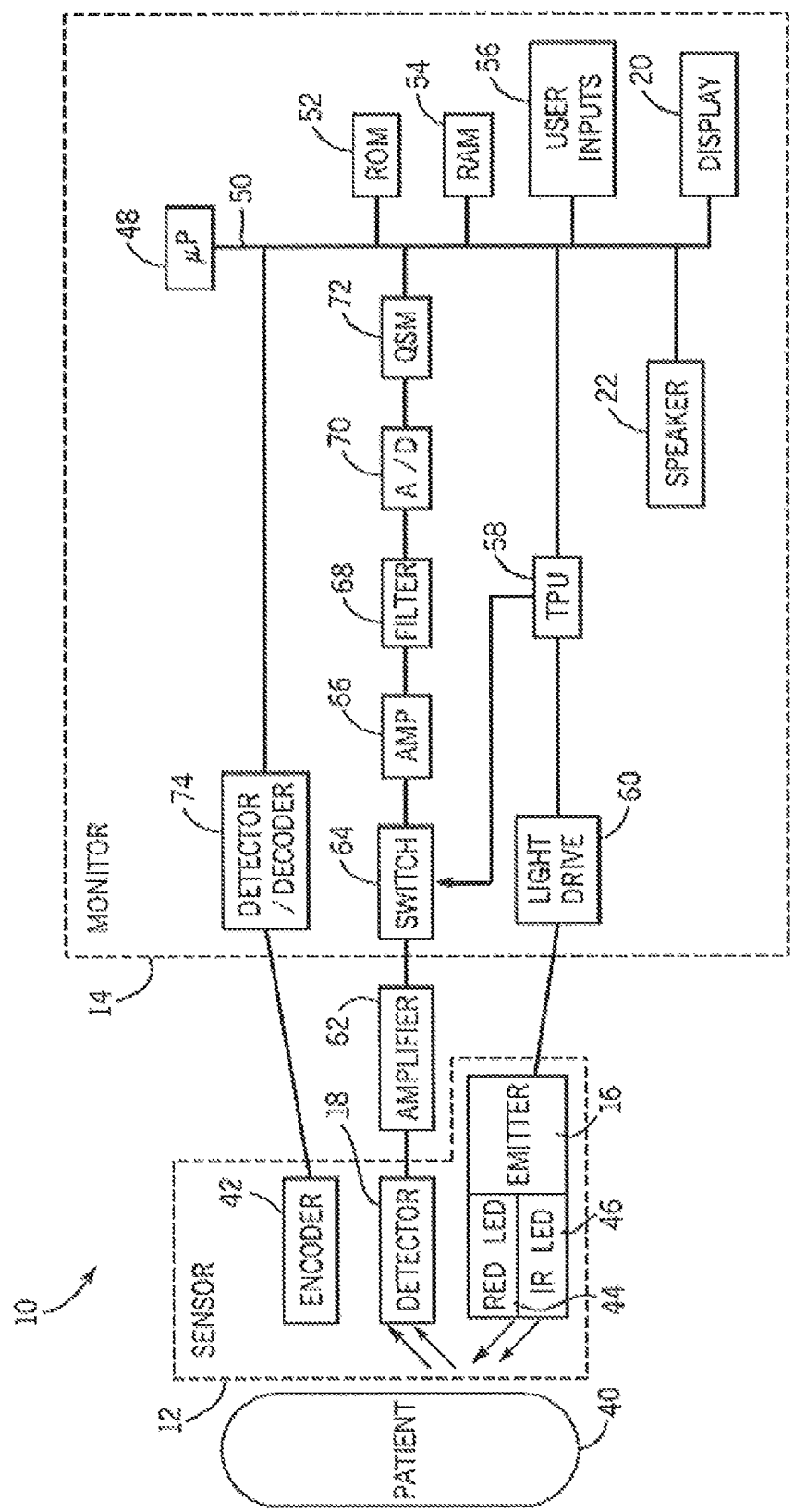
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an approach, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an approach, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an approach, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an approach, microprocessor 48 may determine the patient's physiological parameters, such as SpO$_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an approach, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals. PPG signals may be taken herein to mean processed or filtered PPC signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found) for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
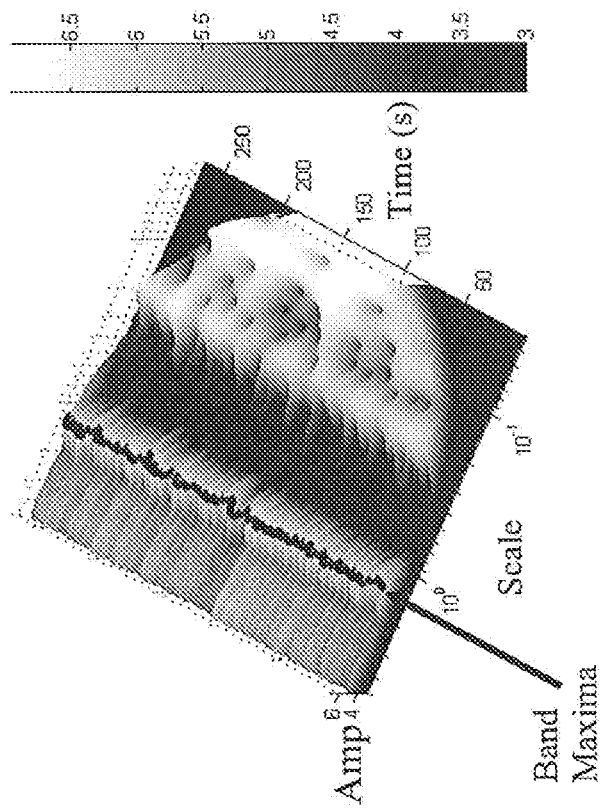
FIGS. 3(a) and 3(b) show illustrative views of a scalogram derived from a PPG signal in accordance with an embodiment.
Figure 3A:
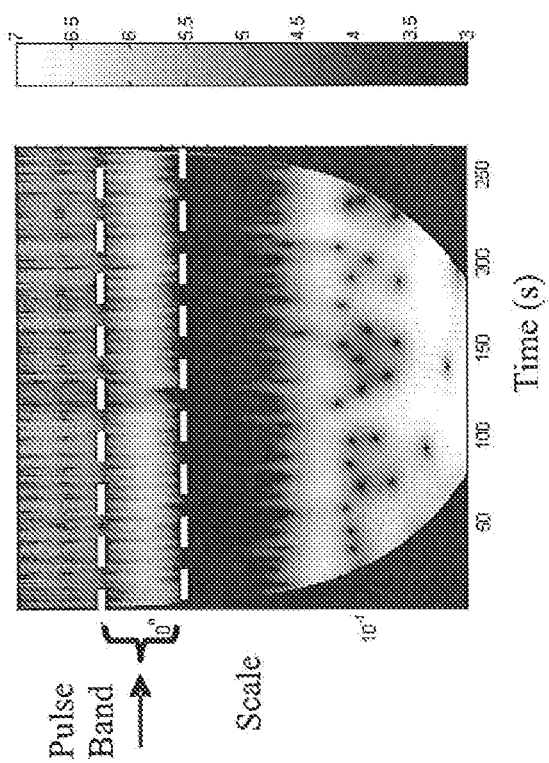

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
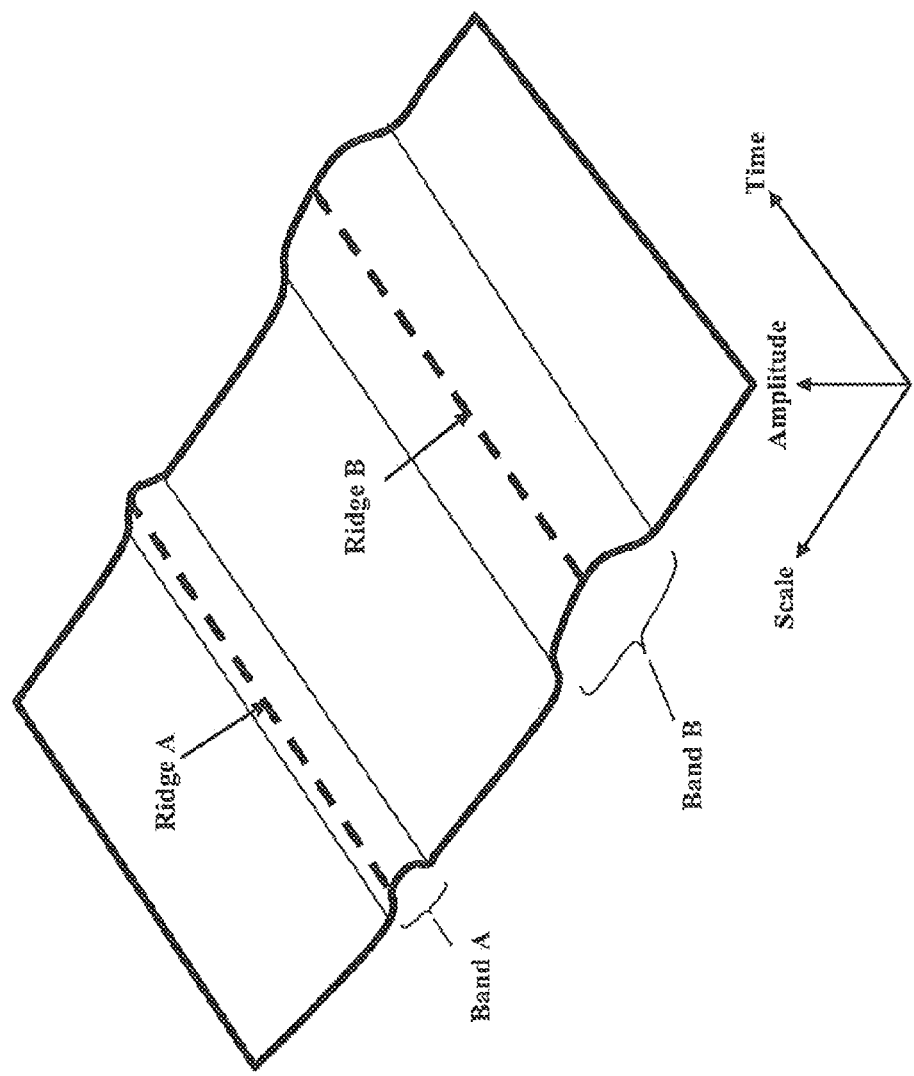
FIG. 3(c) shows an illustrative scalogram derived from a signal containing two pertinent components in accordance with an embodiment.
Figure 3D:
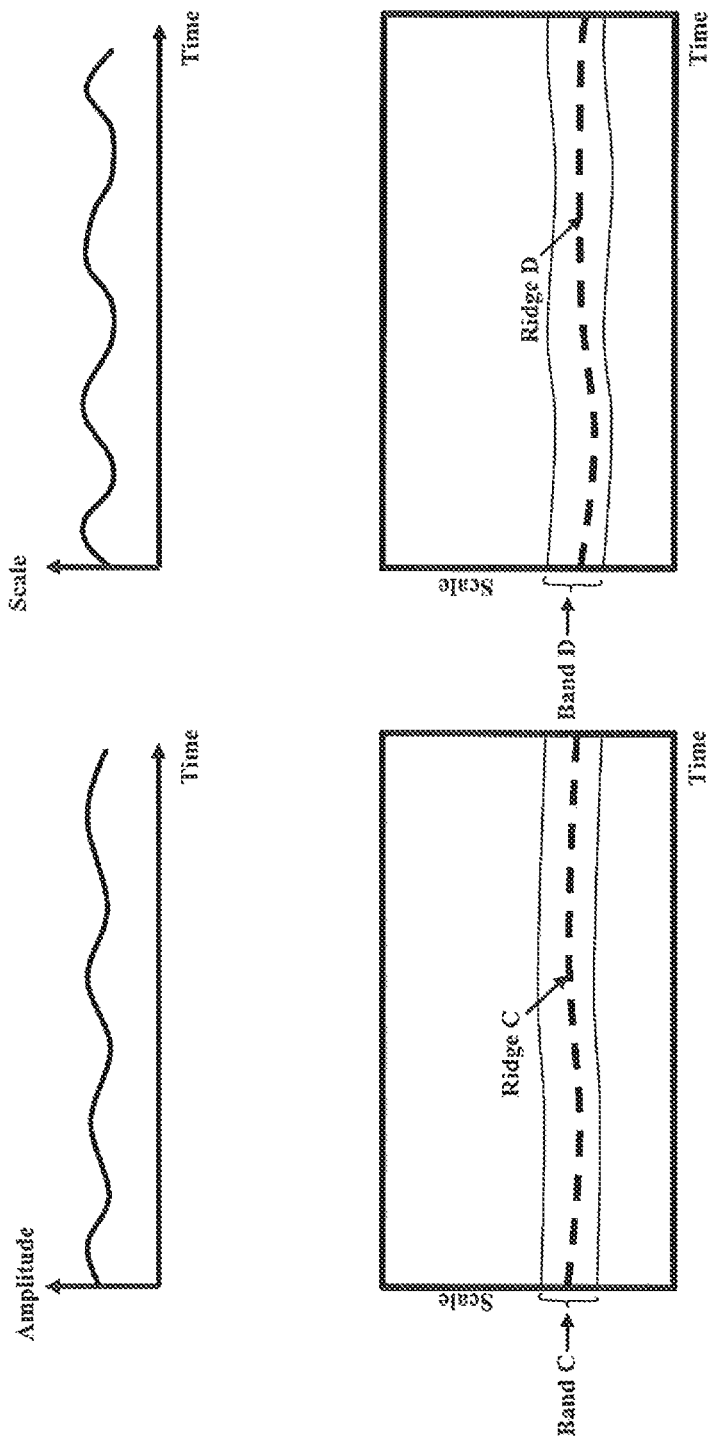
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a, b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^\infty \frac{|\hat{\psi}(f)|^2}{f} df \qquad (17)$$

Figure 3E:
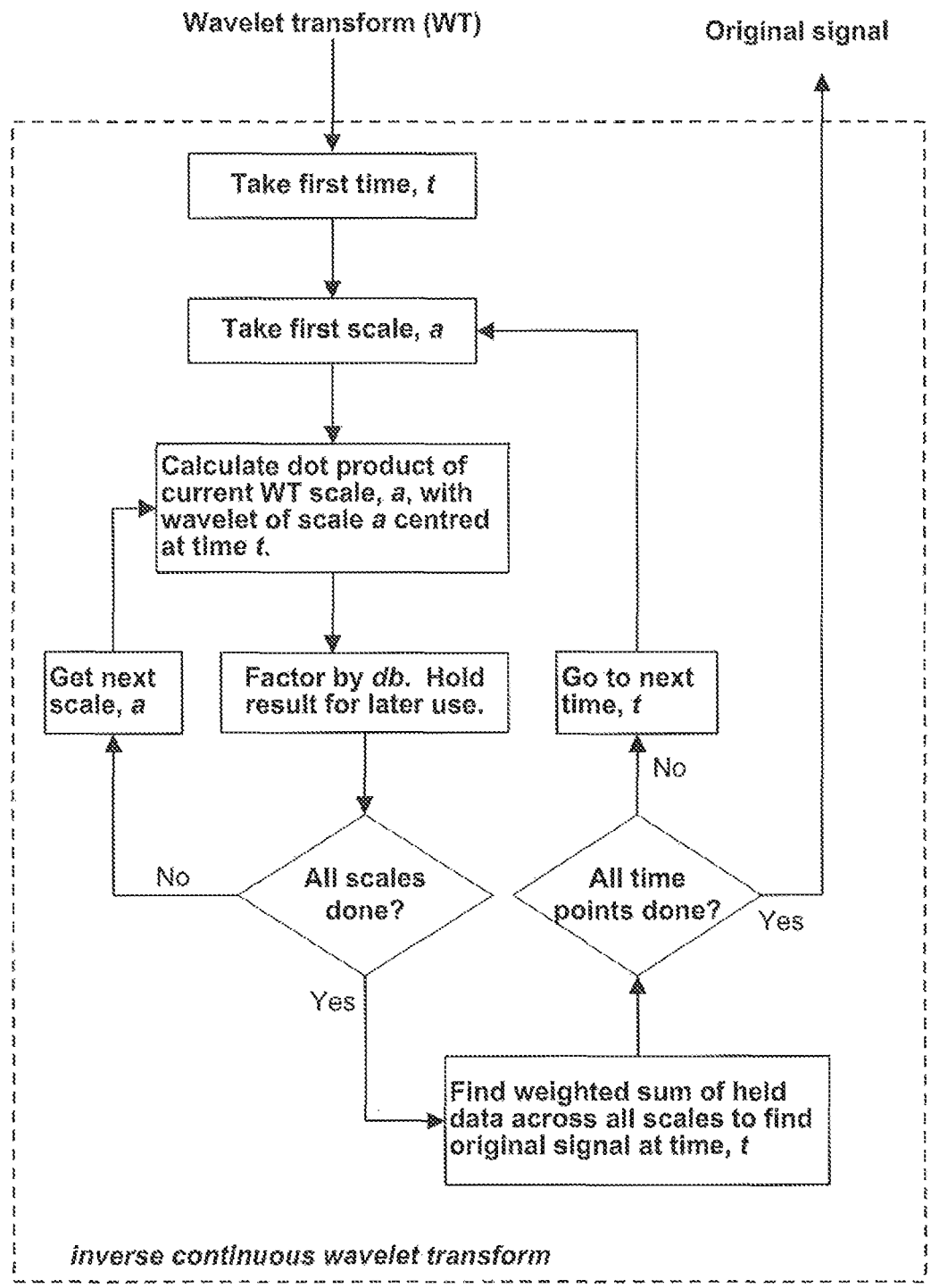
FIGS. 3(e) and 3(f) are flow charts of illustrative steps involved in performing an inverse continuous wavelet transform in accordance with embodiments.
Figure 3F:
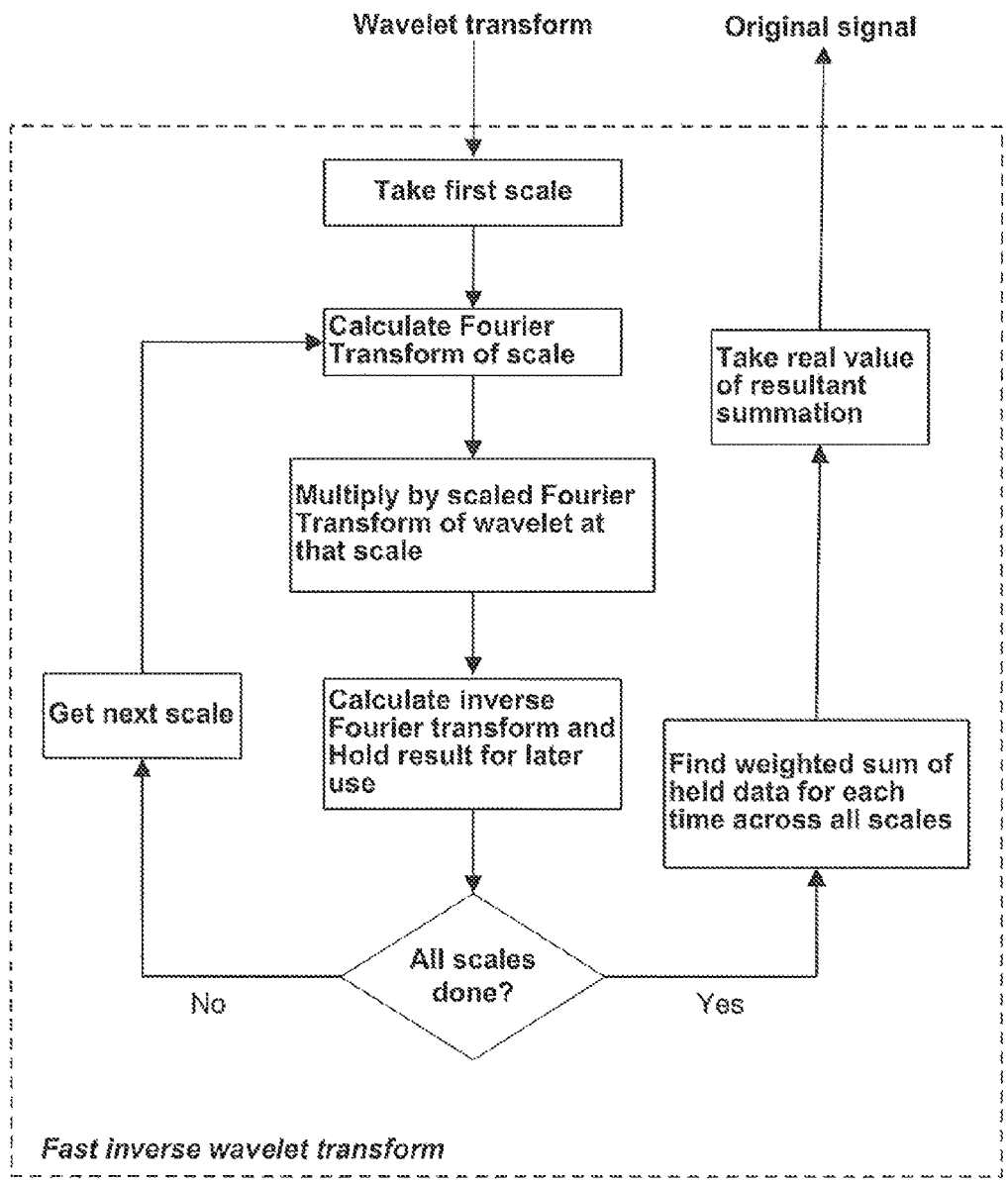

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
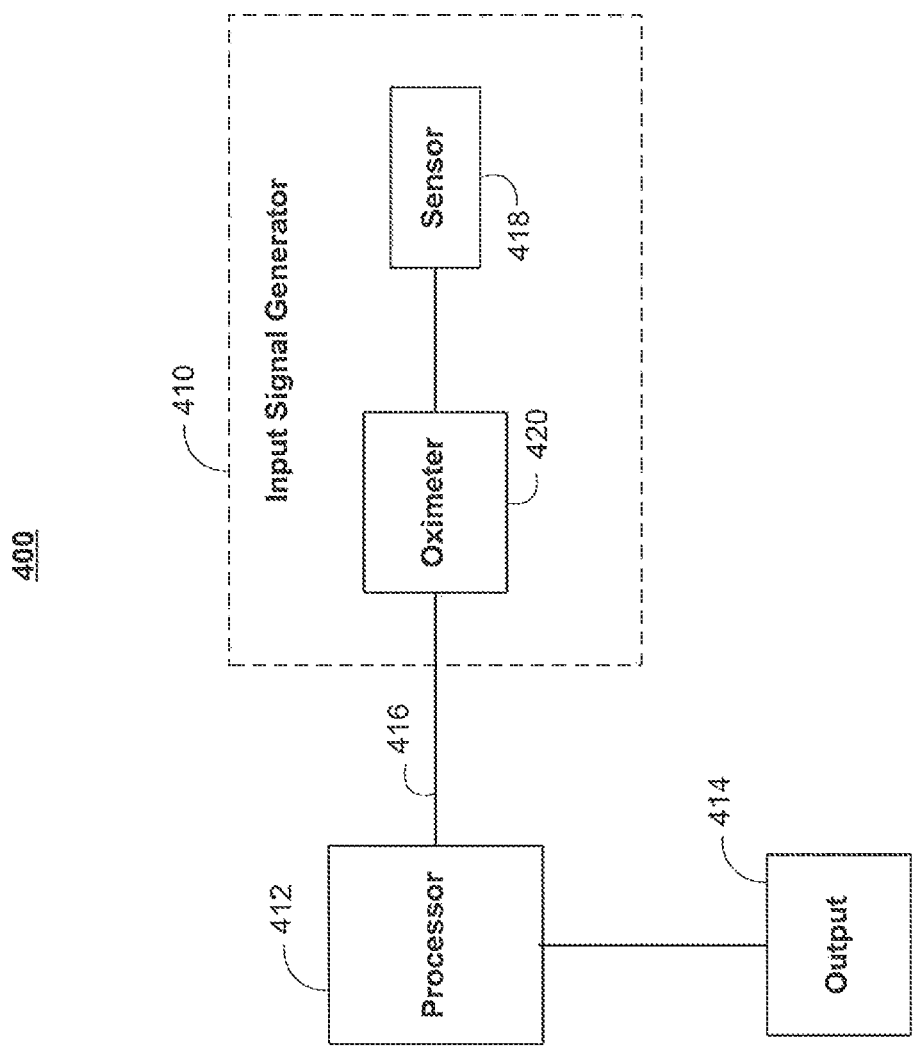
FIG. 4 is a block diagram of an illustrative continuous wavelet processing system in accordance with an embodiment.

FIG. 4 is an illustrative continuous wavelet processing system in accordance with an embodiment. In this embodiment input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
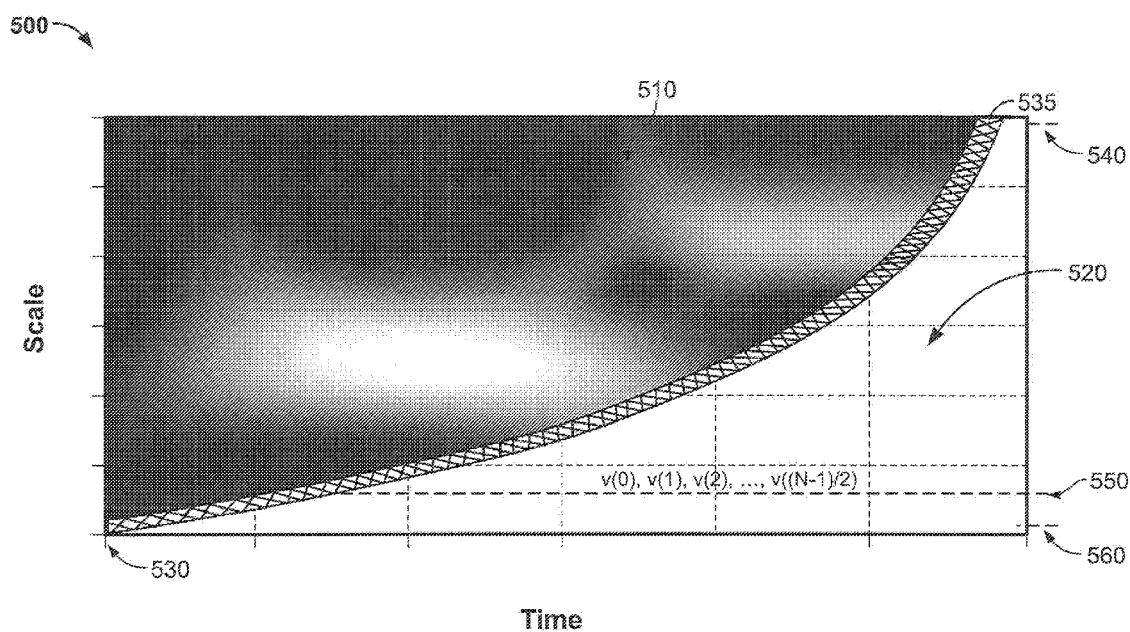
FIG. 5 is an illustrative plot of a scalogram that may be obtained from a PPG signal in accordance with an embodiment.

FIG. 5 is an illustrative plot of a scalogram that may be obtained from a photoplethysmograph (PPG) signal in accordance with an embodiment. Scalogram 500 may be generated in pulse oximetry system 10 (FIG. 1) using, for example, a processor such as processor 412 (FIG. 4) or microprocessor 48 (FIG. 2). In scalogram 500, the horizontal axis denotes time and the vertical axis denotes scale. The darkness of the shading of a point in scalogram 500 denotes the relative energy value of the scalogram at that point. Scalogram 500 may be a processed version of a preliminary scalogram that has been, for example, filtered, cleaned, smoothed, or otherwise manipulated prior to display. The PPG signal from which scalogram 500 is generated may be obtained from a patient such as patient 40 (FIG. 2), using a sensor such as sensor 12 (FIG. 1). Alternatively, the PPG signal may be obtained by averaging or otherwise combining multiple signals derived from a suitable sensor array, as discussed in relation to FIG. 1. Scalogram 500 may be displayed using any suitable display device such as, for example, monitor 20 (FIG. 1), display 28 (FIG. 1), a PDA, a mobile device, or any other suitable display device. Additionally, scalogram 500 may be displayed on multiple display devices.

Scalogram 500 may include resolved region 510 and wedge region 520. Wedge region 520 may appear in the right side of scalogram 500, and may represent a region of unresolved or partially resolved scalogram values. Wedge region 520 may correspond to a region in which future values of an underlying PPG signal are needed to fully resolve scalogram energy values. For example, in an approach, the infinite future (and/or past) values of an underlying PPG signal may be needed to fully resolve scalogram values in wedge region 520 (for example, computation of the Morlet wavelet may require the infinite past and future values of an underlying PPG signal). Alternatively, rather than an infinite PPG signal, an operator or processor may be used to determine a required length of a PPG signal (including a length of past values and/or future values) to sufficiently "resolve" scalogram 500. The required length of the PPG signal, may depend on an application and/or on the biological characteristics of a patient such as patient 40 (FIG. 2), and this information may be stored, for example, in ROM 52 (FIG. 2) or RAM 54 (FIG. 2). For example, an operator may determine the length of section of future signal values needed from the underlying PPG signal so that the error between a fully resolved wavelet transform and a computed wavelet transform is acceptable for a given application, which may include determining a patient respiration rate, oxygen saturation level, and/or respiration effort level. In an approach, the Morlet wavelet (or any other infinite-length wavelet) is computed using a section of an underlying signal, for example, an underlying PPG signal, that is of finite length, for example, having three standard deviations from the center of a Gaussian window forming part of the wavelet function, and longer or shorter sections of the underlying signal may also be used to resolve values in scalogram 500.

Typically, the length of the required section of past and/or future PPG values depends on the scale value for which the scalogram is being resolved, with larger scales (smaller values on the vertical axis) requiring larger sections of the underlying PPG signal to be resolved. Therefore, wedge region 520 may, in practice, closely resemble a wedge shape, as shown in FIG. 5. However, in an alternative arrangement, wedge region 520 may appear as any other suitable shape. The energy values of scalogram 500 within wedge region 520 (i.e., energy values that have yet to be resolved) may appear discontinuous from those in resolved region 510. For example, energy values in wedge region 520, if estimated by, for example pulse oximetry system 10 (FIG. 1), may include spurious or erroneous features, including additive noise. Therefore, in an approach, the scalogram values in wedge region 520 may be set to predetermined low-energy values set by a user or operator prior to display, for example, on monitor 26 (FIG. 1) or display 20 or 28 (both of FIG. 1). Alternatively, and as shown in FIG. 5, the energy values of the scalogram in wedge region 520 may be set to an undefined value (for example, to the value "NaN") and/or may not be displayed, leading to a wedge-like shape in a scalogram such as scalogram 500.

One or more patient parameters may be determined based on interpolating, extrapolating, and/or extracting characteristics of scalogram 500. For example, the oxygen saturation, respiration rate, and/or respiration effort level of a patient such as patient 40 (FIG. 2) may be determined using, for example, processor 412 (FIG. 4) or microprocessor 48 (FIG. 2).

In an approach, characteristics of scalogram 500 may be used to identity and/or filter noise or interference in the underlying PPG signal used to generate scalogram 500. In this scenario, inaccurate estimates of scalogram 500 in wedge region 520 may degrade the detection and/or estimation of these parameters (or of other physiological parameters of patient 40 (FIG. 2)). Alternatively, if scalogram values in wedge region 520 are undefined to avoid potentially inaccurate estimates, as shown in FIG. 5, then the extracted parameter values may be based on old and/or outdated scalogram data, which may lead to outdated and/or ineffective estimates of a signal parameter or parameters, such as those of patient 40 (FIG. 2). For example, if scalogram values in wedge region 520 are undefined, a patient respiration rate may be computed based only on scalogram values occurring prior to time 530 (as scalogram energy values in wedge region 520 may be ignored). This approach may yield outdated parameter calculations if the time-rate of change of the patient respiration rate is sufficiently rapid.

Therefore, it may be desired to use wedge region 520 of the scalogram to compute parameter estimates or extract relevant parameters, such as the parameters of patient. For example, improved techniques for estimating true scalogram values at various locations within wedge region 520 may be desired. In an approach, an improved estimate of scalogram values at a scale value, for example, scale value 550, may be determined by computing a convolution of a wavelet with an acquired signal, for example, an acquired PPG signal. In an approach, scalogram energy values in wedge region 520 may be determined by computing multiple convolutions of various wavelets (where each wavelet corresponds to a particular scale value) with the acquired signal. In this way, estimates of scalogram energy values in wedge region 520 may be continuous with those in resolved region 510. In an approach, estimates of the scalograms at scale 550 may also rely on information from the physiological system producing the underlying signal, for example, an acquired PPG signal or any other biosignal. For example, estimation of scalogram 500 value at scale 550 may include parameterization based on known techniques in the art, where parameters may depend on past and/or current characteristics of patient 40 (FIG. 2), room conditions such as temperature and lighting, template matching with existing biological models, and/or on any other suitable technique.

Although the techniques disclosed herein are described in terms of an underlying PPG signal (i.e., from which scalogram 500 is determined), the disclosed techniques may be applied to any other suitable signal. For example, the disclosed techniques may be applied to other biosignals including transthoracic impedance signals, and/or capnograph signals. Further, the PPG signal, or any other signal used to generate scalogram 500, may be obtained from a source other than pulse oximeter system 10 (FIG. 1). For example, the signal may be obtained from another type of medical device or from non-medical devices including a general signal oscilloscope, signal generator, and/or waveform analyzer. Scalogram 500 may be a simplified or idealized embodiment of a scalogram measured in practice. For example, the techniques disclosed herein may be applied to scalogram that have different energy characteristics than those of scalogram 500, including different energy amplitude values, noise patterns, and/or discontinuous features.

Figure 6:
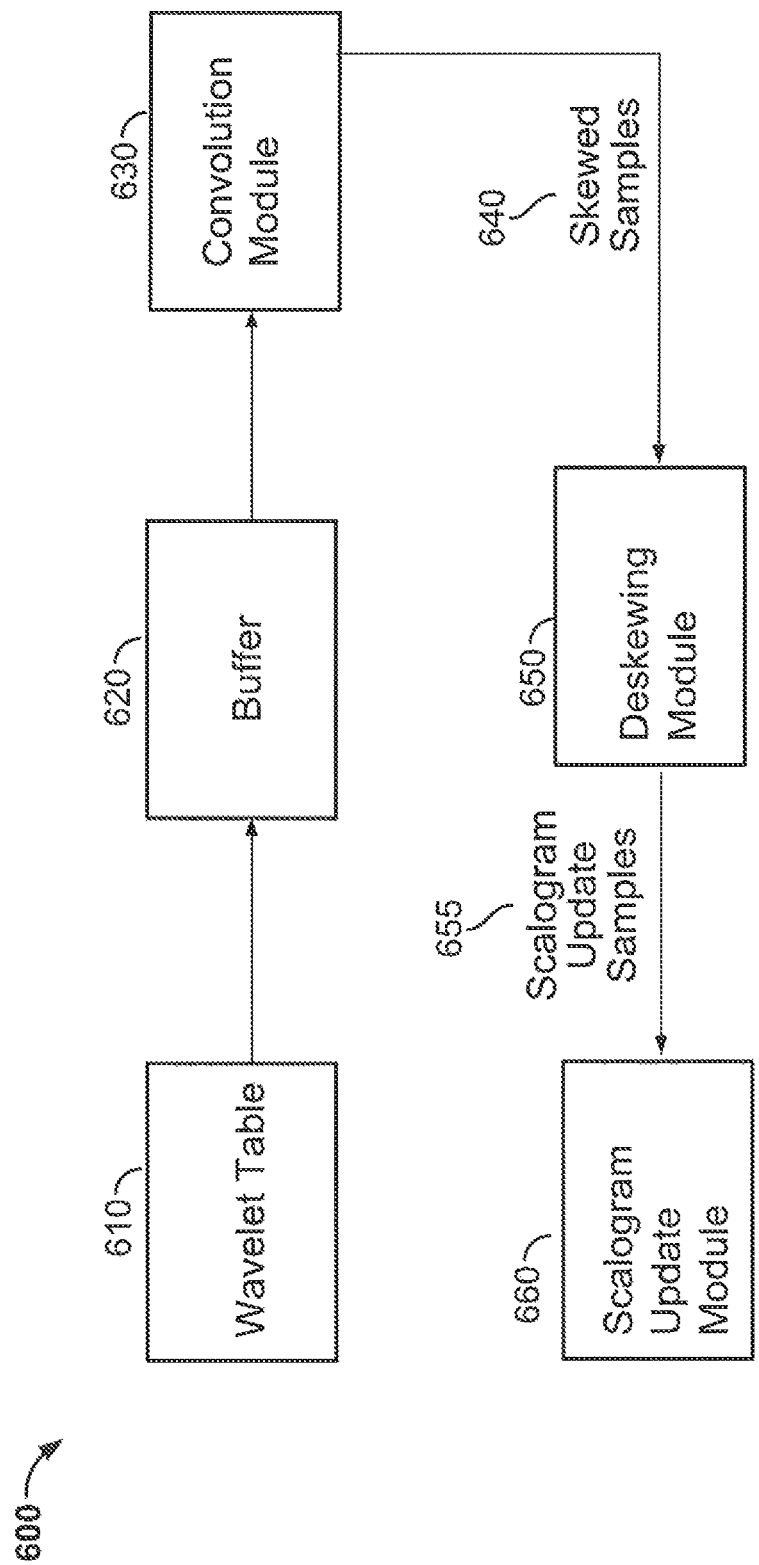
FIG. 6 is a block diagram of a system that may be used for generating a scalogram, including a resolved region and a wedge region, in accordance with an embodiment.

FIG. 6 is a block diagram of a system that may be used for generating a scalogram, the scalogram including a resolved region and a wedge region, in accordance with an embodiment. System 600 may be used to generate a scalogram such as scalogram 500 (FIG. 5). System 600 may generate a scalogram, using, for example, processor 412 (FIG. 4) or microprocessor 48 (FIG. 2), by performing a running convolution of incoming signal samples with a series of normalized wavelets, each corresponding to a different scale value. System 600 may include wavelet table 610 for storing the normalized wavelets, for example, in a matrix structure. Wavelet table 610 may be logical and/or actual representation of memory locations including, for example, within ROM 52 (FIG. 2) or RAM 54 (FIG. 2). In an approach, the memory locations of wavelet table 610 may be accessed using a processor such as processor 412 (FIG. 4) or microprocessor 48 (FIG. 2). The values stored in wavelet table may correspond to predetermined wavelet coefficients that are hardcoded into one or more components of pulse oximetry system 10 (FIG. 1). Alternatively, the values stored in wavelet table 610 may be input to pulse oximetry system 10 (FIG. 1), using, for example, flash memory or other solid state memory technology, optical storage including CD-ROM or DVD storage, magnetic storage devices including magnetic cassettes, magnetic tape, and magnetic disk storage, and/or any other medium which can be used to store the desired information and which can be accessed by one or more components of the pulse oximetry system 10 (FIG. 1).

System 600 may include a buffer that may be similar or identical to input signal buffer 620, which may store or contain a set of signal samples. For example, buffer 620 may contain a set of Q recent samples from a PPG signal, where Q is a positive integer. In an approach, an input PPG signal may be sampled uniformly (i.e., at a constant or substantially constant rate), and buffer 620 may store the most recent Q samples. In an approach, the samples stored in buffer 620 may be stored in memory locations of ROM 52 (FIG. 2) or RAM 54 (FIG. 2), and may be accessed using a processor such as processor 412 (FIG. 4) or microprocessor 48 (FIG. 2). In an approach, the samples contained in buffer 620 may be continually updated as the underlying PPG signal evolves in time and additional samples of the PPG signal are taken.

System 600 may include a convolution module similar or identical to convolution module 630. Convolution module 630 may be used to perform a running convolution of incoming signal samples, stored, for example, in buffer 620, with the series of normalized wavelets, stored in wavelet table 610. In an approach, convolution module 630 may perform a matrix multiplication on wavelet table 610, having dimensions N Q, with buffer 620, having dimensions Q 1, where N is a positive integer. In an approach, the dimensions associated with each of these parameters may refer to logical (that is, matrix representation) dimensions, physical dimensions in a memory such as ROM 52 (FIG. 2) or RAM 54 (FIG. 2), or to both. The matrix multiplication may be performed using a processor such as processor 412 (FIG. 4) or microprocessor 48 (FIG. 2), and the results of the matrix multiplication may be stored in, for example, ROM 52 (FIG. 2) or RAM 54 (FIG. 2). Alternatively, convolution module 630 may use another technique to convolve an incoming PPG signal with a table of wavelet coefficients, such as wavelet table 610. For example, convolution module 630 may use dedicated convolution hardware and/or software, and/or may use algorithms for iteratively performing a convolution operation or convolution-like operation without performing any explicit matrix multiplications.

The output of convolution module 630, may be a set of Q scalogram energy samples corresponding, for example, to PPG input signal values stored in buffer 620. For example, skewed samples 640 may represent Q scalogram energy values that may be used to perform an incremental update of a scalogram. For example, as shown in FIG. 5, skewed samples 640 may correspond to scalogram update samples 535 of scalogram 500 (both of FIG. 5). However, skewed samples 640 may first need to be deskewed before being added to a scalogram such as scalogram 500 (FIG. 5). This is because, in an approach, scales within a wavelet table, for example, wavelet table 610, may be misaligned with respect to a corresponding scalogram, for example, scalogram 500 (FIG. 5). For example, the scales in wavelet table 610 may be centered in time (for example, within a corresponding matrix), and this may result in a delay in the output of scalogram values corresponding to smaller scales relative to those corresponding to larger scale values. Thus, convolution module 630 may slide each wavelet to the edge of an array in the matrix corresponding to a given scale value using, for example, processor 412 (FIG. 4) or microprocessor 48 (FIG. 2), so that signal components with smaller features are output with minimal delay. This approach may result in the output of convolution module 630 (i.e., skewed samples 640) being skewed in time. For example, in an approach, smaller features of the skewed samples 640 may appear to have occurred sooner in time than larger features (i.e., a lack of horizontal/time alignment). As a result, skewed samples 640 may need to be deskewed before being added to a scalogram, for example, as scalogram update samples 535 of scalogram 500 (both of FIG. 5).

System 600 may include a deskewing module similar or identical to deskewing module 650. Deskewing module 650 may be used to align skewed samples 640 to produce scalogram update samples 655, which are suitable for addition to a scalogram such as scalogram 500 (FIG. 5). For example, deskewing module 650 may map each scale value in skewed outputs 640 to an appropriate position, for example, time-position, in scalogram 500, with samples added in time from right to left. In an approach, deskewing module 650 may produce scalogram update samples 535 (FIG. 5) when system 600 operates on scalogram 500 (FIG. 5). System 600 may include a scalogram update module 660. Scalogram update module 660 may be used to add a computed portion of updated scalogram values to an existing scalogram. For example, scalogram update module 660 may add scalogram update samples 655 to a scalogram such as scalogram 500 (FIG. 5) by writing to memory (e.g., ROM 52 (FIG. 2) and/or RAM 54 (FIG. 2)) the values of scalogram update samples 655. In an approach, scalogram update module 660 may add scalogram update samples 655 to scalogram 500 (FIG. 5) in the time and location positions shown in FIG. 5. Scalogram update module may, for example, read scalogram update samples 655 from ROM 52 (FIG. 2) or RAM 54 (FIG. 2) and may write scalogram update samples 655 to different memory location positions in ROM 52 (FIG. 2) or RAM 54 (FIG. 2), or to other memory locations in pulse oximetry system 10 (FIG. 1). In an approach, scalogram 500 (FIG. 5) is updated at a certain rate. For example, in an approach, a certain number scalogram updates are performed every minute, and system 600 may be instantiated with a corresponding rate to perform these updates.

Figure 7:
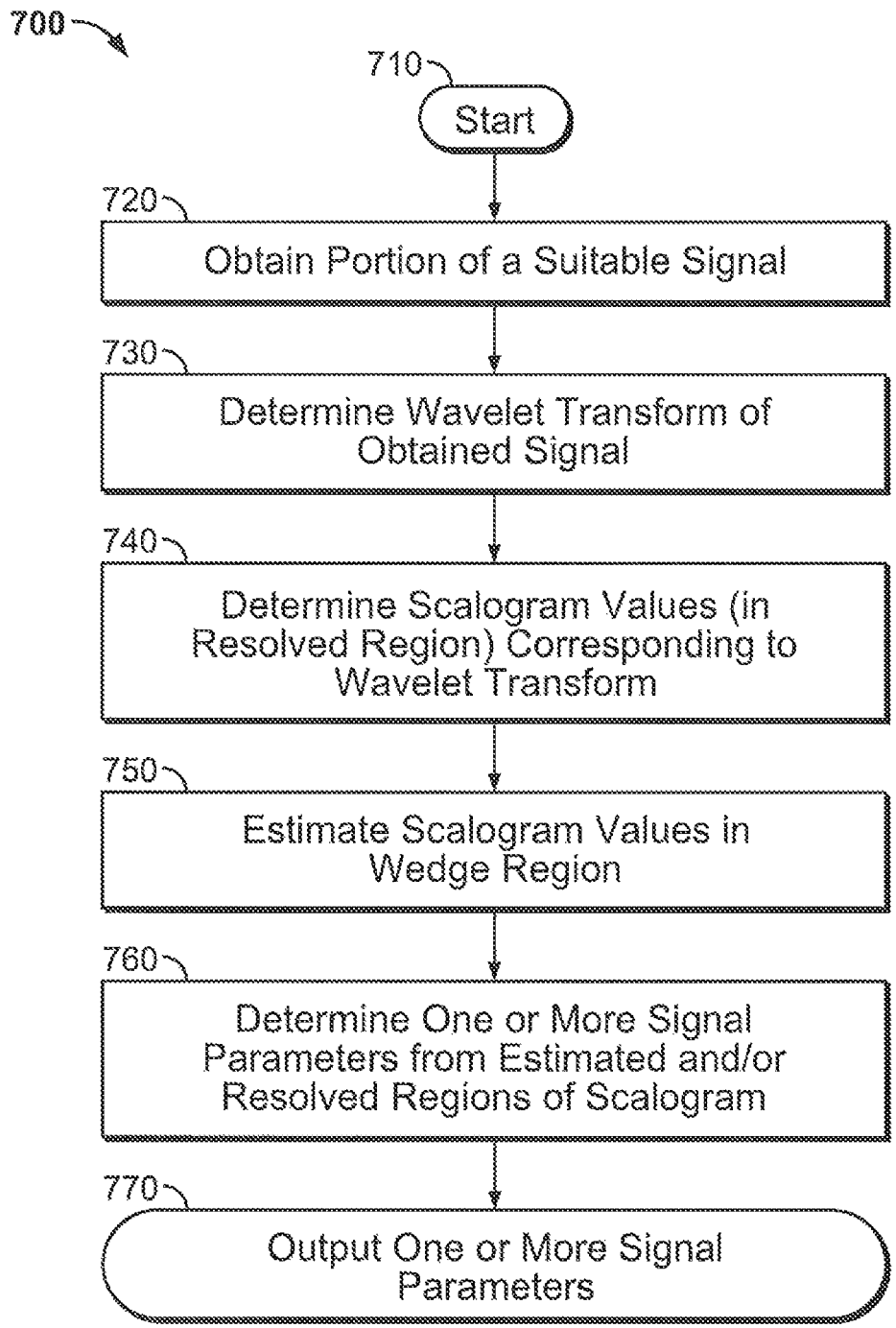
FIG. 7 shows illustrative steps for estimating scalogram values in a wedge region in accordance with an embodiment.

FIG. 7 shows illustrative steps for estimating scalogram values in a wedge region, for example, wedge region 520 (FIG. 5) in accordance with an embodiment. Process 700 may start at step 710. At step 720, a portion of a suitable signal may be obtained, for example, using pulse oximetry system 10 (FIGS. 1 and 2) or system 400 (FIG. 4). The signal obtained at step 720 may be a PPG signal, or as described earlier, another suitable signal. At step 730, a continuous wavelet transform of the signal obtained at step 720 may be obtained. At step 740, a scalogram of the continuous wavelet transform may be generated or otherwise obtained. For example, the scalogram of the wavelet transform may be generated or obtained using a processor such as processor 412 (FIG. 4) or microprocessor 48 (FIG. 2) and the computed scalogram may be displayed on a monitor such as monitor 26 (FIG. 1) or display 20 or 28 (both of FIG. 1).

At step 750, scalogram values in a wedge region, for example, wedge region 520 of scalogram 500 (both of FIG. 5) may be determined. For example, process 700 may determine an updated set of scalogram values (e.g., similar or identical to scalogram update samples 535 of FIG. 5) using techniques similar or identical to those described in relation to system 600 (FIG. 6). For example, process 700 may use any suitable convolution-based technique to estimate scalogram values in a wedge region such as wedge region 520 (FIG. 5). In an approach, process 700 may, at step 750, use processes and techniques similar to those described in relation to FIGS. 8 and 9 to estimate scalogram energy values in a wedge region. In addition, the estimation scheme used at step 750 may depend on one or more system parameters, and may be set manually by an operator using, for example, user inputs 56 (FIG. 2), or automatically, for example, by pulse oximetry monitor 14 (FIG. 1), or through a combination thereof. In an approach, parameters of the estimation scheme used at step 750 may depend on the biological characteristics of patient 40 (FIG. 2). For example, estimation of scalogram values in wedge region 520 (FIG. 5) may be performed by pulse oximetry monitor 14 (FIG. 1) using processor 412 (FIG. 4) or microprocessor 48 (FIG. 2). The estimated values of the scalogram may be displayed on a monitor or display such as monitor 26 (FIG. 1) or display 20 or 28 (both of FIG. 1). Step 750 may produce a "complete" scalogram, where the complete scalogram includes the scalogram obtained at step 730 with some or all energy values in a wedge region, for example, wedge region 520 (FIG. 5), replaced by the estimated scalogram values obtained at step 750.

At step 760, one or more signal parameters may be determined based on the resolved portion of the scalogram obtained at step 740 and the estimated portion of the scalogram obtained at step 750. For example, signal parameters corresponding to the biological characteristics of patient 40 (FIG. 2) may be determined, including oxygen saturation, respiration rate, and/or respiration effort. In an approach, noise parameters and/or noise characteristics of the signal obtained at step 710 may be determined at step 760. For example, noise parameters may be determined by applying one or more filters or any suitable processing technique to the complete scalogram, by using template matching, averaging, and/or any other suitable technique. In an approach, noise may be removed from the complete scalogram or directly from the signal obtained at step 710, based on the determined noise parameters and/or noise characteristics.

At step 770, the one or more signal parameters determined at step 760 may be output. For example, the signal parameters may be output to a display such as monitor 26 (FIG. 1) or display 20 or 28 (both of FIG. 1), through an audible message provided through a speaker such as speaker 22 (FIG. 2), through a written printout, or through a combination of some of these and other suitable techniques.

Figure 8:
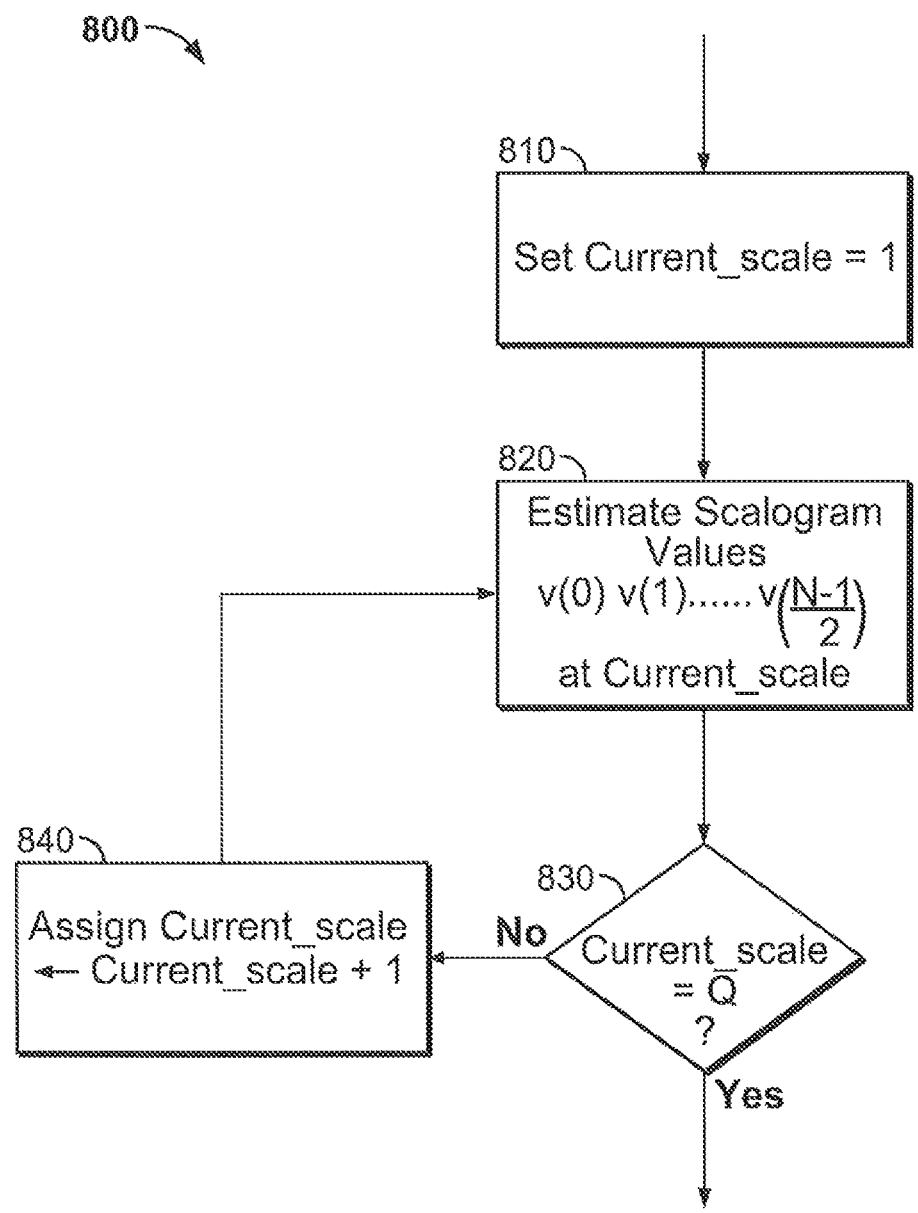
FIG. 8 shows illustrative steps for estimating scalogram values in a wedge region by enumerating over a set of estimation locations in accordance with an embodiment.

FIG. 8 shows illustrative steps for estimating scalogram values in a wedge region, for example, wedge region 520 (FIG. 5), by enumerating over a set of estimation locations in accordance with an embodiment. Process 800 may correspond to a further embodiment of step 750 of process 700 (both of FIG. 7) and may be used for estimating scalogram energy values over various locations in the wedge region. Process 800 may be used to enumerate over scale values in a wedge region, such as wedge region 520 (FIG. 5), and may be used together with a convolution-based estimation scheme, or convolution-like estimation scheme, at each particular scale value. In an approach, process 800 may enumerate over Q scale values.

At step 810, a scale counter, current_scale, may be set to a value of one, indicating that a first scale value in the scalogram (for example, scalogram 500 of FIG. 5) has been chosen. In an approach, the first scale value may correspond to a smallest scale value (that is, the largest scale value on the vertical axis in the scalogram). For example, current_scale may initially be set to scale value 540 (FIG. 5) and this may be denoted by setting current_scale equal to the value one.

At step 820, scalogram energy values in the scale range corresponding to current_scale may be estimated. For example, scalogram values may be determined at a total of $$\frac{N+1}{2}$$

points, where N is a positive integer denoting the total number of sampled signal values needed to fully determine (i.e., resolve) the scalogram to sufficient accuracy. In general, the value of N may depend on the current scale value, and larger scale values (i.e., smaller values of the scalogram vertical axis) may correspond to a larger value of N. Scalogram energy values at scale value current_scale may be estimated using any suitable technique, including any suitable convolution-based or convolution-like technique. For example, scalogram energy values may be estimated using the convolution-based estimation technique described in relation to FIG. 9, below.

At step 830, the value of current_scale may be compared to a maximum value, for example, to the value Q. If the value of current_scale is equal to the maximum value, then the scalogram, for example, scalogram 500 (FIG. 5), has been estimated at all target scale values. If, however, the value of current_scale is not equal to this maximum value, then process 800 may have only estimated scalogram values at a subset of all desired scale values, and may proceed to step 840. For example, in an approach, the value of current_scale may correspond to scale value 550 (FIG. 5). In this case, process 800 may proceed to step 840. At step 840, the value of current scale may be incremented, and process 800 may return to step 820. At step 820, scalogram energy values in the scale range corresponding to the new value of current_scale (i.e., assigned at step 840) may be estimated using techniques similar or identical to those described above.

Figure 9:
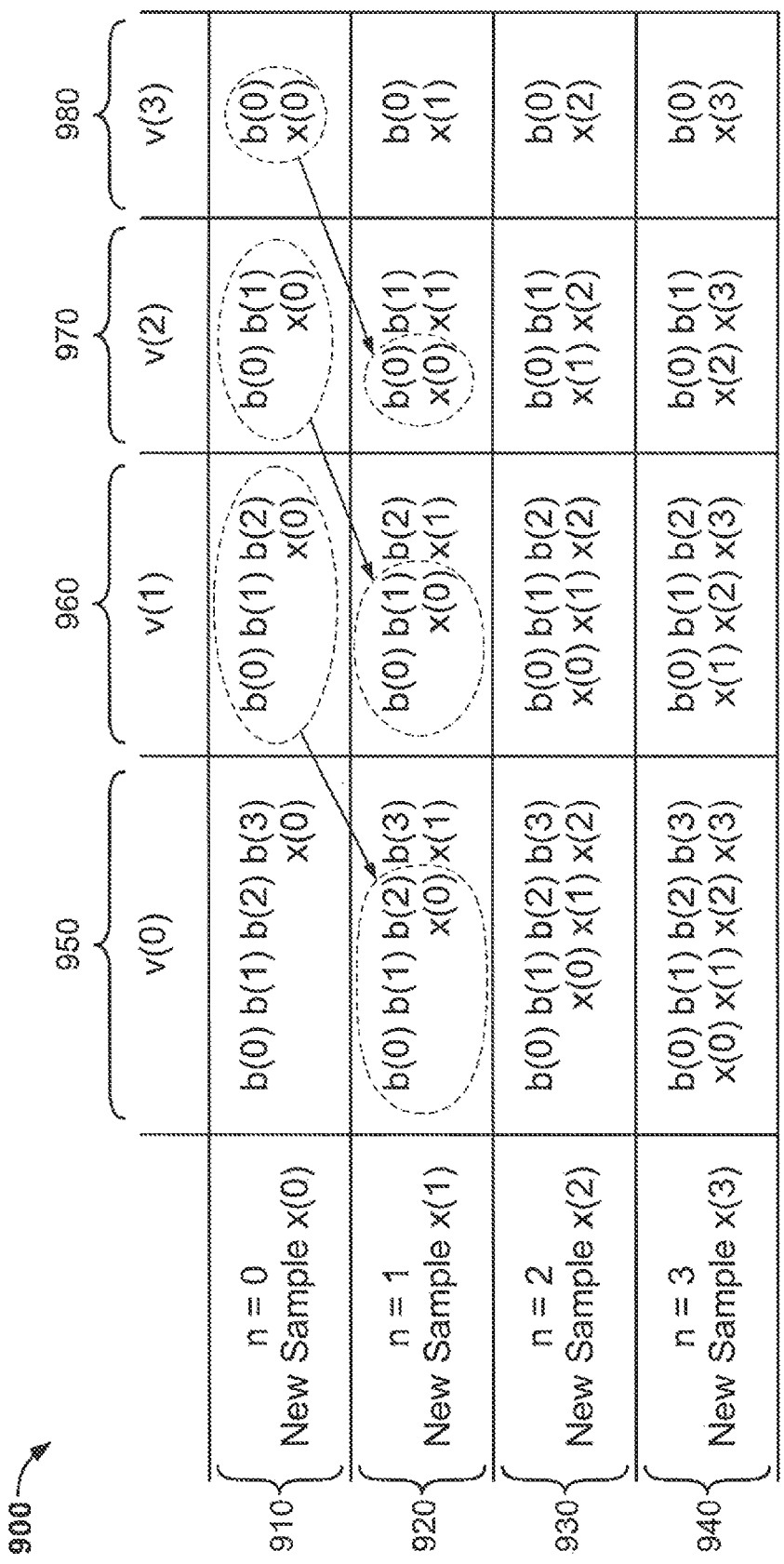
FIG. 9 depicts an illustrative technique for estimating energy values at a particular scale value in a wedge region of a scalogram in accordance with an embodiment.

FIG. 9 depicts an illustrative technique for estimating energy values at a particular scale value in a wedge region of a scalogram (for example, at scale value 550 of scalogram 500) in accordance with an embodiment. Process 900 may correspond to a further embodiment of step 820 of process 800 (both of FIG. 8). In an approach of process 900, estimated values within the wedge region may gradually become more accurate (that is, match more closely the true value of the scalogram) as estimates are taken from right to left. In an approach, the techniques of process 900 may be used to produce continuously more accurate values of a scalogram, that gradually equal the actual value of the scalogram, as estimates are, for example, made closer to the boundary between a resolved region, for example, resolved region 510 (FIG. 5) and a wedge region, for example, wedge region 520 (FIG. 5).

Process 900 may compute scalogram estimates a particular scale value, for example at scale value 540, 550, or 560 (all of FIG. 5), as follows. For example, that a total of N−1)/2 scalogram points are to be estimated and added to a scalogram at a particular scale value. The estimates may be labeled v(0), v(1), . . . , v((N−1)/2), where v(0) is the left-most estimate location (that is, the estimation location closest to the resolved region) and v((N−1)/2) is the right-most estimate location (that is, the estimation location furthest from the resolved region), as shown at scale value 550 of FIG. 5. In an approach, a total of N scalogram values may be estimated, and estimated scalogram values v(0), v(1), . . . , v((N−1)/2) may be added to the scalogram, for example, using scalogram update module 660 (FIG. 6). In an approach, b(0), b(1), . . . , b(N−1) may denote the wavelet table coefficients corresponding to the current scale. For example, b(0), b(1), . . . and b(N−1) may be the values stored in wavelet table 610, in the row (and/or set of memory locations) corresponding to the current scale value. In an approach, x(0), x(1), . . . and x(N−1) may denote a set of consecutive input signal samples.

Time 910 denotes a time period in which only signal sample x(0) is available. In this case, process 900 may compute estimates v(0), v(1), . . . , v(N−1) as follows $$v(N-1)=x(0)b(0), \quad (18A)$$

$$v(N-2)=x(0)b(1), \quad (18B)$$

$$v(N-3)=x(0)b(2), \quad (18C)$$

$$\ldots$$

$$v(0)=x(0)b(N-1). \quad (18D)$$

Next, time period 920 denotes a time period in which signal samples x(0) and x(1) are available. With new sample x(1), estimates v(0), v(1), ..., v(N−1) may be updated, and calculated as $$v(N-1)=x(1)b(0), \quad (19A)$$

$$v(N-2)=x(0)b(0)+x(1)b(1), \quad (19B)$$

$$v(N-3)=x(0)b(1)+x(1)b(2), \quad (19C)$$

$$\ldots$$

$$v(0)=x(0)b(N-2)+x(1)b(N-1). \quad (19D)$$

This approach can be further extended to the time where signal sample x(N−1) has been received, as $$v(N-1)=x(N-1)b(0),$$

$$v(N-2)=x(N-2)b(0)+x(N-1)b(1),$$

$$v(N-3)=x(N-3)b(0)+x(N-2)b(1)+x(N-1)b(2),$$

$$\ldots$$

$$v(0)=x(0)b(0)+x(1)b(1)+x(N-1)b(N-1).$$

In an approach, only the values v(0) through v(N−1)/2) are placed into a corresponding scalogram, for example, scalogram 500 (FIG. 5). Further, when updating the scalogram, for example, scalogram 500 (FIG. 5) with the new data v(0) through v((N−1)/2), the old (i.e., existing) values of the scalogram may be shifted to the left. Using a technique similar or identical to the one described above, estimates in a scalogram wedge region (for example, wedge region 520 of scalogram 500, both of FIG. 5), may be simplified as previous calculations may be used to calculate current and future values. For example, when sample x(1) is received, the estimation updates (eqns. 19A-19D) may be written in terms of the initial estimates (eqns. 18A-18D) as follows:

$$v(N-1)=x(1)b(0), \quad (20A)$$

$$v(N-2)=v(N-1)_{x=0}+x(1)b(1), \quad (20B)$$

$$v(N-3)=v(N-2)_{x=0}+x(1)b(2), \quad (20C)$$

$$\ldots$$

$$v(0)=v(1)_{x=0}+x(1)b(N-1), \quad (20D)$$

where $v(1)_{x=0}$ denotes the value of the estimate v(1), at a time x=0 (i.e., at time 910 in FIG. 9). Further, eqns. 20A-20D may be applied each time after a new sample has been received to compute updated scalogram values. For example, in an approach, eqns. 20A-20D may be used to derive scalogram update samples 535 (FIG. 5).

Process 900 shows a simplified illustration in which a total of four scalogram points are to be estimated and added to at a particular scale in a scalogram in a wedge region. In an approach, process 900 may be used to estimate scalogram values at a scale 550 (FIG. 5) when N=4, that is, when the points v(0), v(1), ..., v(3) are to be estimated. At time 910, a sample x(0) of a signal, for example, a PPG signal, is obtained. As shown in FIG. 9, with only one sample available, scalogram estimates at time 910 are given by $$v(3)=x(0)b(0), \quad (21A)$$

$$v(2)=x(0)b(1), \quad (21B)$$

$$v(0)=x(0)b(2), \text{ and} \quad (21C)$$

$$v(0)=x(0)b(3). \quad (21D)$$

At time 920, a second sample, x(1), is received. As shown in FIG. 9, in each of columns 950, 960, 970, and 980, previous sample x(0) is (logically) shifted to the left, and sample x(1) is placed in the right-most position in each column. The scalogram estimates at time 920, are thus $$v(3)=x(1)b(0), \quad (22A)$$

$$v(2)=x(0)b(0)+x(1)b(1), \quad (22B)$$

$$v(1)=x(0)b(1)+x(1)b(2), \text{ and} \quad (22C)$$

$$v(0)=x(0)b(2)+x(1)b(3). \quad (22D)$$

Note at time 920, that the results of computations performed at time 910 can be used to simplify (that is, lessen) the number of computations required at time 920. For example, the computation performed in column 980 at time 910 may be reused as a partial computation required at time 920 in column 970. Similarly, the computation performed in column 970 at time 910 may be reused as a partial computation required at time 920 in column 960, and the computation performed in column 960 at time 910 may be reused as a partial computation required at time 920 in column 950.

Process 900 may continue as described above at times 930 and 940. As seen in FIG. 9, at each consecutive time step, an additional signal sample is used in determining a scalogram estimate. At time 940, the estimate of v(3) is computed using all of the wavelet coefficients, for example, stored in wavelet table 610 (FIG. 6). That is, as seen in FIG. 9, the estimate of v(3) at time 930 is $$v(3)=x(0)b(0)+x(1)b(1)+x(2)b(2)+x(3)b(3), \quad (23)$$

which relies on all wavelet coefficients corresponding to the particular scale in use. Therefore, at time 940, the value of v(3) in eqn. (23) is fully resolved, and is no longer an estimated value. A process similar to the process described above may be used to estimate scalogram values at each scale in a wedge region of a scalogram.

It will be understood that, while the above disclosure is made in the context of a medical signal processing application (i.e., based on one or more PPG signals generated by a pulse oximetry system), the features of the present disclosure may be applied in the context of any signal processing application and may be applied to any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

It will also be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for processing a scalogram, the method comprising:
    receiving a signal from a signal generator;
    using processing equipment for:
        sampling the signal to generate a set of samples,
        generating the scalogram based at least in part on a continuous wavelet transform of the set of samples,
        updating the set of samples with at least one new sample of the signal to generate an updated set of samples,
        convolving the updated set of samples with wavelet coefficients to produce skewed scalogram samples, wherein the skewed scalogram samples are skewed in time relative to the scalogram,
        deskewing the skewed scalogram samples to produce scalogram update samples, wherein deskewing comprises aligning the skewed scalogram samples in time relative to the scalogram,
        updating the scalogram by adding the scalogram update samples to the scalogram, and
        determining information from the signal based at least in part on the updated scalogram; and
    outputting the information to an output device.

2. The method of claim 1, wherein the signal comprises a photoplethysmograph (PPG) signal.

3. The method of claim 2, wherein the information comprises a patient respiration rate.

4. The method of claim 2, wherein the information comprises a patient oxygen saturation level.

5. The method of claim 2, wherein the information comprises a patient respiration effort level.

6. The method of claim 2, wherein the sampling is performed at a substantially constant time-rate.

7. The method of claim 1, wherein the updating is performed at a refresh rate that depends at least in part on an expected time-rate of change of at least one patient parameter.

8. The method of claim 1, wherein the output device comprises a display.

9. The method of claim 1, wherein the convolving is performed at least in part by at least one processor, and wherein the at least one processor performs one or more matrix multiplications.

10. The method of claim 1, wherein the wavelet coefficients correspond to a truncated Morlet wavelet.

11. The method of claim 1, wherein the wavelet coefficients are stored in a wavelet table and wherein the wavelet coefficients for at least two scales are misaligned in time.

12. The method of claim 1, wherein the skewed scalogram samples comprise samples for at least two scales and wherein the deskewing comprises mapping the skewed scalogram samples for each scale to a different time position to produce the scalogram update samples.

13. A system for processing a scalogram, the system comprising:
    a sensor for receiving a signal from a signal generator;
    one or more processors coupled to the sensor, wherein the one or more processors are configured to:
        sample the signal to generate a set of samples,
        generate the scalogram based at least in part on a continuous wavelet transform of the set of samples,
        update the set of samples with at least one new sample of the signal to generate an updated set of samples,
        convolve the updated set of samples with wavelet coefficients to produce skewed scalogram samples, wherein the skewed scalogram samples are skewed in time relative to the scalogram,
        deskew the skewed scalogram samples to produce scalogram update samples, wherein the skewed scalogram samples are deskewed by aligning the skewed scalogram samples in time relative to the scalogram,
        update the scalogram by adding the scalogram update samples to the scalogram, and
        determine information from the signal based at least in part on the updated scalogram; and
    an output device configured to output the information.

14. The system of claim 13, wherein the signal comprises a photoplethysmograph (PPG) signal.

15. The system of claim 14, wherein the information comprises a patient respiration rate.

16. The system of claim 14, wherein the information comprises a patient oxygen saturation level.

17. The system of claim 14, wherein the information comprises a patient respiration effort level.

18. The system of claim 14, wherein the sampling is performed at a substantially constant time-rate.

19. The system of claim 13, wherein the updating is performed at a refresh rate that depends at least in part on an expected time-rate of change of at least one patient parameter.

20. The system of claim 13, wherein the output device comprises a display.

21. The system of claim 13, wherein the convolving is performed at least in part by at least one processor, and wherein the at least one processor performs one or more matrix multiplications.

22. The system of claim 13, wherein the wavelet coefficients correspond to a truncated Morlet wavelet.

23. The system of claim 13, wherein the wavelet coefficients are stored in a wavelet table and wherein the wavelet coefficients for at least two scales are misaligned in time.

24. The system of claim 13, wherein the skewed scalogram samples comprise samples for at least two scales and wherein the deskewing comprises mapping the skewed scalogram samples for each scale to a different time position to produce the scalogram update samples.

* * * * *